(12) United States Patent
Raedts

(10) Patent No.: US 9,089,793 B2
(45) Date of Patent: Jul. 28, 2015

(54) FILTER SYSTEM

(75) Inventor: Marcellus Johannes Hubertus Raedts, Emmen (NL)

(73) Assignee: JEMP HOLDING BV, Emmen (NL)

( * ) Notice: Subject to any disclaimer, the term of this patent is extended or adjusted under 35 U.S.C. 154(b) by 1333 days.

(21) Appl. No.: 12/299,429

(22) PCT Filed: May 19, 2007

(86) PCT No.: PCT/NL2007/000131
§ 371 (c)(1),
(2), (4) Date: Nov. 14, 2008

(87) PCT Pub. No.: WO2007/136247
PCT Pub. Date: Nov. 29, 2007

(65) Prior Publication Data
US 2009/0071888 A1 Mar. 19, 2009

(30) Foreign Application Priority Data

May 19, 2006 (NL) ..................................... 1031843

(51) Int. Cl.
*B01D 15/20* (2006.01)
*B01D 15/22* (2006.01)
*G01N 30/56* (2006.01)
*G01N 30/60* (2006.01)

(52) U.S. Cl.
CPC .............. *B01D 15/206* (2013.01); *B01D 15/22* (2013.01); *G01N 30/56* (2013.01); *G01N 30/6004* (2013.01)

(58) Field of Classification Search
CPC .. B01D 15/206; B01D 15/22; G01N 30/6004; G01N 30/56
USPC ............... 210/198.2, 656, 659, 189, 281, 282
See application file for complete search history.

(56) References Cited

U.S. PATENT DOCUMENTS

| | | | | |
|---|---|---|---|---|
| 2,902,162 | A | * | 9/1959 | Humbert, Jr. et al. ......... 210/438 |
| 4,711,276 | A | * | 12/1987 | Simonazzi ..................... 141/286 |
| 5,213,683 | A | * | 5/1993 | Mann ........................... 210/198.2 |
| 5,653,885 | A | * | 8/1997 | Jameson et al. ............... 210/634 |
| 5,667,676 | A | * | 9/1997 | Alaska ......................... 210/198.2 |
| 5,714,074 | A | * | 2/1998 | Karlsson et al. .............. 210/656 |
| 5,718,281 | A | * | 2/1998 | Bartalone et al. .............. 165/41 |
| 6,095,202 | A | * | 8/2000 | Colon et al. .................... 141/34 |
| 6,402,958 | B1 | * | 6/2002 | Moran .......................... 210/656 |

(Continued)

FOREIGN PATENT DOCUMENTS

| | | |
|---|---|---|
| CA | 2563157 | 11/2005 |
| EP | 0310867 | 4/1989 |

(Continued)

OTHER PUBLICATIONS

International search report in corresponding PCT/NL2007/000131.

*Primary Examiner* — Ernest G Therkorn
(74) *Attorney, Agent, or Firm* — Young & Thompson

(57) ABSTRACT

A chromatography column to bind molecules or proteins, is filled with a replaceable matrix and is provided with fill elements with which a single feed tube can be connected to an across the column distributed fill element. The fill element keeps an inner land area free from fill openings which can be closed. With the fill element it is possible to dispense the matrix into the column in an equally spread manner. Elements are present to internally flush the feed tube, while there are features to make the flushing impossible during filling with matrix.

8 Claims, 8 Drawing Sheets

(56) References Cited

U.S. PATENT DOCUMENTS

| | | | |
|---|---|---|---|
| 6,719,899 B2 * | 4/2004 | Davis et al. | 210/198.2 |
| 7,704,388 B2 * | 4/2010 | Chi et al. | 210/198.2 |
| 7,718,058 B2 * | 5/2010 | Agee et al. | 210/198.2 |
| 2003/0098280 A1 * | 5/2003 | Davis et al. | 210/656 |
| 2004/0182776 A1 * | 9/2004 | Raedts | 210/411 |
| 2006/0266684 A1 * | 11/2006 | Pichl | 210/198.2 |
| 2007/0000833 A1 * | 1/2007 | Levy et al. | 210/435 |
| 2007/0090035 A1 * | 4/2007 | Rahn et al. | 210/198.2 |
| 2007/0138100 A1 * | 6/2007 | Hofmann et al. | 210/656 |

FOREIGN PATENT DOCUMENTS

| | | |
|---|---|---|
| EP | 0696223 | 1/2000 |
| WO | 9922234 | 5/1999 |
| WO | 03059488 | 7/2003 |
| WO | 2004103517 | 12/2004 |
| WO | 2005105256 | 11/2005 |

* cited by examiner

FILTER SYSTEM

REFERENCE TO RELATED APPLICATIONS

This application is a 371 of PCT/NL07/00131 filed May 19, 2007.

This invention relates to a filter system to filter a substance from a gas or liquid. Particularly the invention relates to a chromatography column, e.g. to filter or bind molecules or proteins. More particularly the invention relates to filling the relevant filter system with filter medium. In the following this filter medium will be called filling, matrix or resin.

U.S. Pat. No. 6,576,124, U.S. Pat. No. 6,402,958, U.S. Pat. No. 6,257,416 and WO 03/059488 A3 disclose for this field relevant state of the art and their contents are incorporated in here by reference.

The object of the invention is versatile. A possible first object of the invention is, to guarantee a homogeneous filling of the filter system with the matrix, such that, a.o., the filter system will function better. A possible second object is to automate the tilling, such that the costs of filling and the risk of contamination of the matrix become smaller. Further possible objects will become clear from the following.

According to the invention the filter system is therefore provided with filling means with which a single feed tube is connectable to a filling member which is distributed across the filter system. The filling member can comprise a single filling opening or a number of mutually spaced filling openings. The filling opening(s) are connected to the space to be filled with the matrix of the filter member of the filter system. It is preferred, that the filling element keeps an internal land area (e.g. in relation with a doughnut or torus like filter member to be filled with matrix) free from filling openings and/or that the fill openings are closable by sealing means. Preferably the filling element is designed such that the matrix is equally distributed discharged into the filter member. If with the filter system the matrix is present around a matrix free (core) area (such as with a doughnut or torus like filter member), the filling member preferably extends completely around said matrix free area and comprises e.g. gap like filling opening(s) which preferably provide a possibly closed annular or loop shape.

The sealing means are preferably integrated with the feed tube. Preferably the sealing means are designed such that in a first position they sealingly connect the feed tube to the filter system and simultaneously bring the filling opening(s) in fluid connection with the feed tube, while in a second position they seal the fill openings) and possibly simultaneously sealingly connect the feed tube to the filter system. E.g. the sealing means therefore provide rigid and/or along each other sliding/moving/telescoping parts. The sealing means can in the first position seal at the one, preferably outer side and in the second position at the other, preferably inner side and possibly the one side of the fill opening(s). E.g. the sealing means and/or fill element have (preferably mutually complying) a stepped/changing wall part and/or narrowed sub part or a groove or upright part. In an embodiment the sealing means completely project into the fill opening(s) in the second position and are in the first position completely or partly removed there from.

The sealing means preferably cooperate with the fill means such that it is possible to switch between filling and sealing by mutually movement of parts, such as translating and/or rotating. Thus, at the end of the fill procedure the matrix can be compressed in the filter element.

Preferably the feed tube extends through a supply or discharge opening of the filter system and/or contains the supply or discharge opening. The feed tube possibly extends through a wall in the filter system.

Preferably flushing means are provided to internally flush the feed tube. Preferably means are provided to make flushing impossible during filling with matrix. Preferably flushing is possible in the second position of the above sealing means.

The invention can be applied to virtually each type of filter system, e.g. with the feed and discharge openings of the medium to be filtered and the filtered medium, respectively, to the same side (e.g. (concentrically within each other) or at opposite sides; wherein the medium to be filtered flows from the inside to the outside, or from the outside through the inside, through the filter element; wherein the filter system has a supply and discharge opening for medium to be filtered and has a discharge opening for filtered medium (e.g. according to WO 03/059488A3).

BRIEF DESCRIPTION OF THE DRAWINGS

The invention is further illustrated by way of non-limiting, presently best modes for carrying out the invention embodying examples, while reference is made to the enclosed drawing, in which.

DESCRIPTION OF THE PREFERRED EMBODIMENTS

Figure 1A:
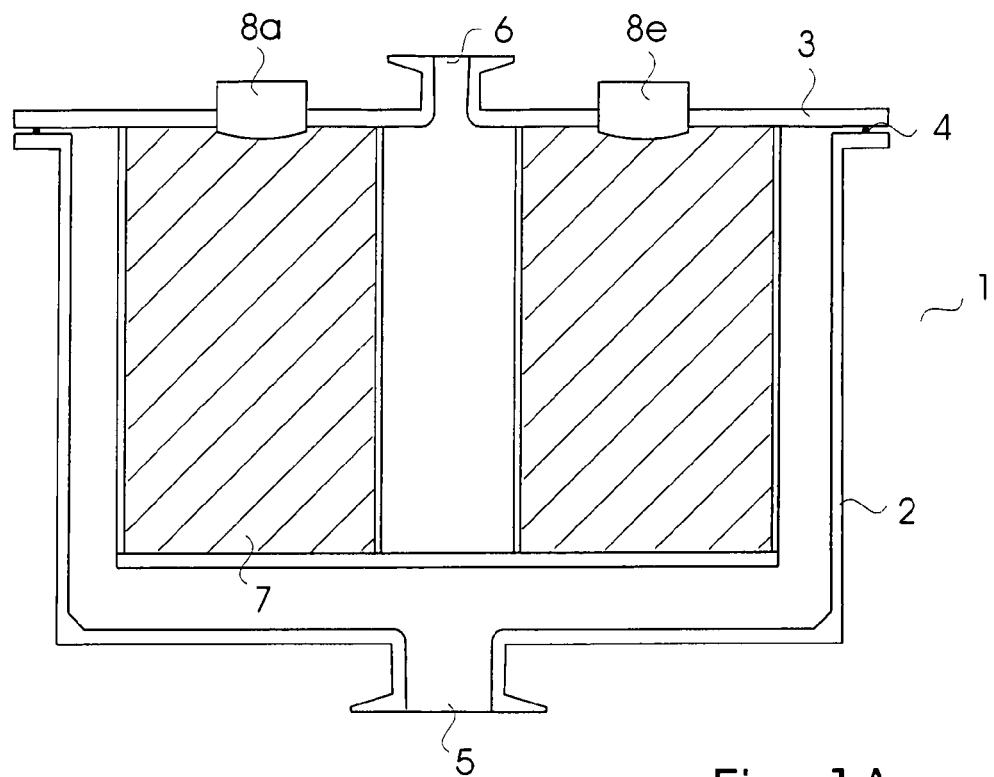
FIGS. 1A and B show a filter system according to the state of the art in sectional side view and top view, respectively.

Elements with an identical, similar or equivalent function or structure are identified by the same reference sign in the drawing.

The drawing shows substantially rotation symmetrical embodiments of the filter element in particular.

Figure 1B:
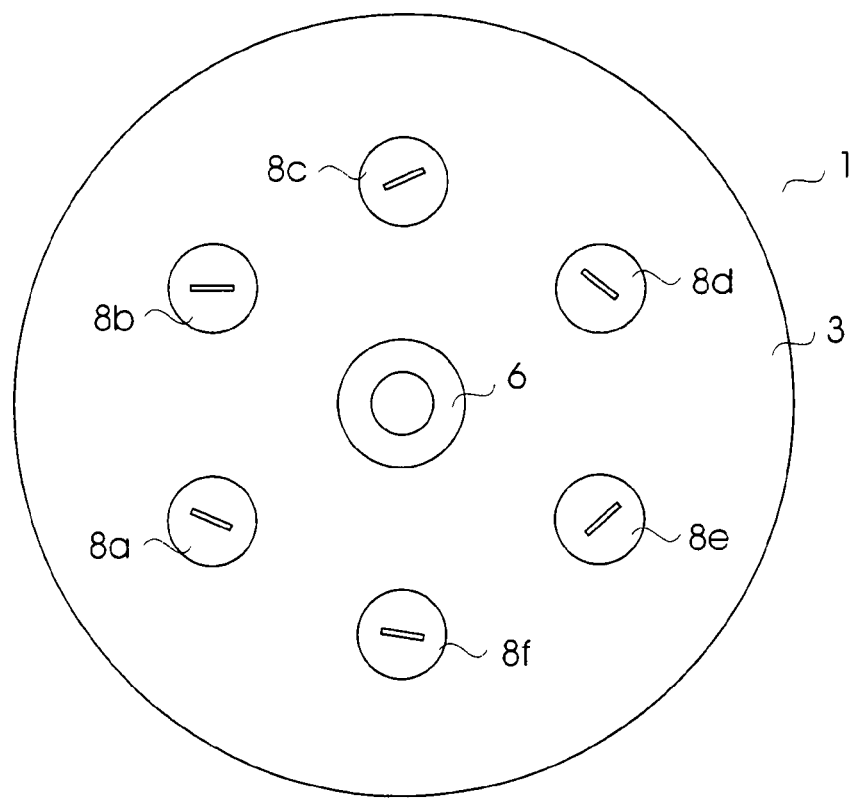

The in FIG. 1 illustrated and according to the prior art fill system has a filter body 1 with a pressure container provided by a pan 2 and a removable lid 3 which, with the aid of an in the drawing not illustrated clamp or mounting system are medium tight kept fixed to each other by interposition of sealing members, such as gasket 4. Via inlet 5 supply of medium to be processed and via outlet 6 discharge of processed medium takes place. Supplied medium flows through the substantially doughnut or torus shaped filter element 7 which is filled with replaceable matrix. The filter element 7 has at the sides facing the openings 5, 6 medium passage blocking (top and bottom) walls, while the (side) walls perpendicular thereto allow passage of medium and block matrix. The side walls are shaped by two concentrically within each other located cases which between them provide the cavity to be filled with matrix. The inner case delimits also at its inner side an inner axial channel that is free from matrix, and which channel is in medium connection with the outlet 6. Between the external case and the axial side wall of the kettle 2 an annular, axial flow space is present. At the side of the top and/or bottom wall of the filter element 7 there is within the filter body 1 above or below, respectively, the filter element 7 a radial flow space connecting to the axial flow space. The medium flows from the inlet 5 in radial direction outward through the radial flow space to subsequently flow through the connecting axial flow space. Then the medium flows through the matrix substantially in the radial direction from the outside to the inside and subsequently flows into the medium free core to subsequently flow in axial direction to the outlet 6. The lid 3 contains fill openings 8a, 8b, . . . 8f, closed with caps. Through said fill openings 8 matrix can be brought into and out the filter element 7 without removing the lid 3. To do that, after removing of the closing caps a dedicated fill hose is connected to each fill opening and matrix is through all fill hoses simultaneously supplied or removed to or from, respectively, the filter element.

According to the invention (viz. FIG. 2-7) with a single feed tube 11 homogeneous filling of the filter element 7 is provided. In the embodiment according to FIG. 2, which is based on FIG. 1, the feed tube 11 projects through the opening 5 and has at its end facing the filter element 7 a widened part 10 provided with sealing means. The side of the filter element 7 facing the opening 5 has a fill opening 9 which runs uninterrupted according to a circuit around the hollow, matrix free core of the filter element 7 and thus separates an internal wall part, substantially overlapping with the matrix free core, of the filter element from the rest of the fill opening 9 containing wall of the filter element. The fill opening 9 is annular in top view, but can also be angled or follow another track, e.g. serpentine. The fill opening 9 can along its length possibly be closed locally, e.g. in that it is constructed from a plurality a mutual spacing maintaining separate openings, e.g. as shown in FIG. 1A.

The sealing means have a the shape of the fill opening 9 in top view following sealing wall which can be inserted into the opening 9.

Figure 2:
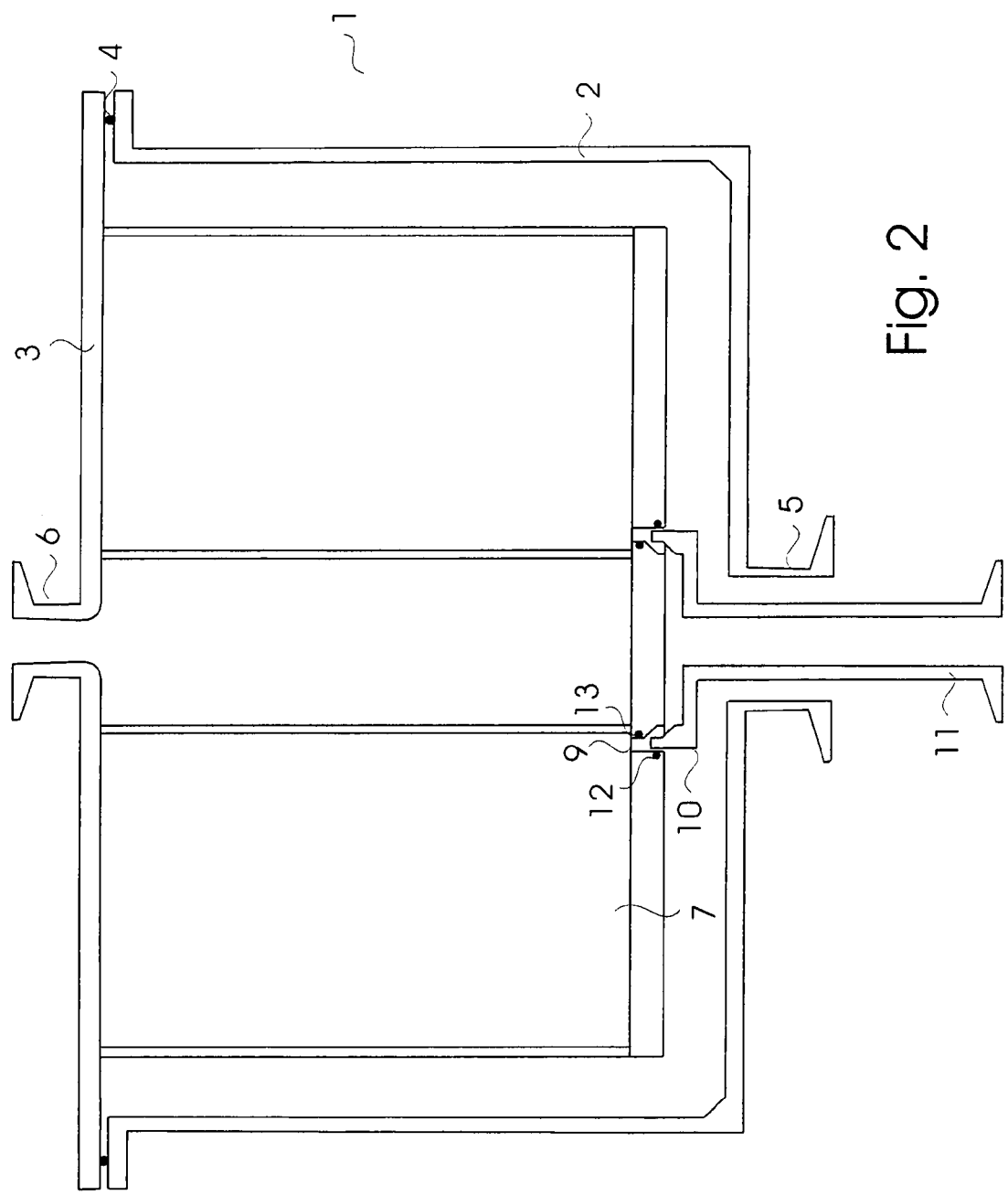
FIGS. 2-4 and 6 show in sectional side view a first, second, third and fourth embodiment according to the invention.

FIG. 2 shows the fill mode. Through the sealing means the fill tube 11 connects medium tight to the wall of the filter element 7 and is through the opened opening 9 in medium connection with the hollow space of the filter element 7 which has to be filled with matrix. The sealing wall partly penetrates into the fill opening 9 and between the mutually facing sides of those two a radially external sealing member 12 is active. By moving the fill tube towards the filter element 7 from the illustrated position, the fill opening 9 is automatically closed by the sealing means at the feed tube 11. For that the opening 9 has, viewed in closing direction of the feed tube 11 (according to the axial direction of the filter element 7) a narrowing. In this example the narrowing is present at the side opposite the feed tube 11. The shape of the sealing means is adapted to the shape of the fill opening 9 and have a narrowing at their sealing wall, which fits into the narrowing of the fill opening.

In the closed position of the feed tube 11, both a radially external sealing member 12 and a radially internal sealing member 13 are active between the mutually facing sides of the sealing wall and the fill opening. Illustrated is that these sealing members 12, 13 are axially at different levels. This is however not required.

As is illustrated, an inclined part connects to the narrowing of the fill opening 9. This can also be a stepped or different shaped part. Preferably the fill opening has a straight radially external wall and the narrowing is provided by a radial change of dimension in the radially internal wall.

It is clear that in the opened position of FIG. 2, the fill opening 9 radially changed dimension. Fill tube 11, widening 10, sealing means and fill opening 9 are shaped such that through feed tube 11 flowing medium flows radially outward when passing the widening 10 and/or fill opening 9 before flowing into the filter element 7.

Figure 8:
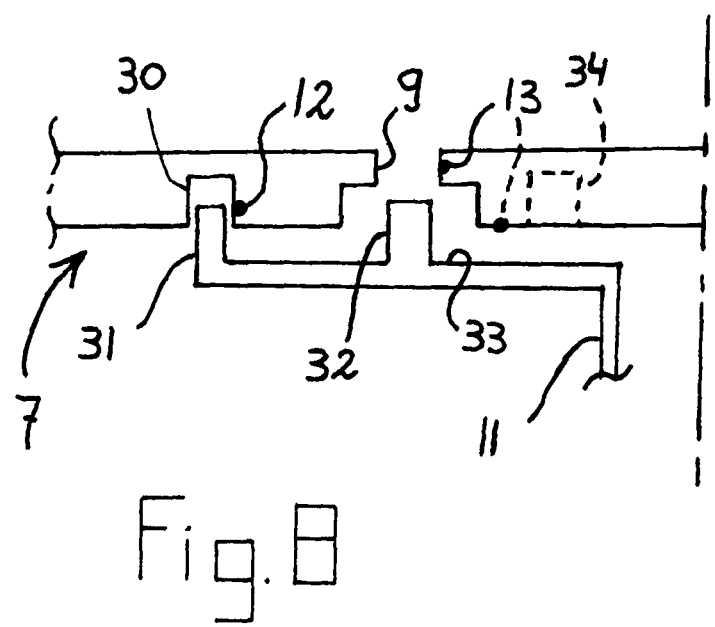
FIG. 8 shows a detail of an alternative for FIG. 2.

An alternative for a permanent medium tight connection of the fill tube 11 to the wall of the filter element 7 is shown in FIG. 8. The wall of the filter element 7 has across a part of its thickness a groove 30 debouching at the side of the fill tube 11 at the radial external side and at a radial distance to the fill opening 9. An in the closing direction of the feed tube 11 extending sealing wall 31 at the feed tube 11 projects into said groove, both in the opened (shown in FIG. 8) and closed position. In that case too, the fill opening 9 is thus at the side facing the feed tube 11 both in the opened and closed position surrounded at its radial outer side by a sealing skirt providing sealing means. The fill opening 9 is narrowed. In the opened position, said narrowed part is released. By moving the feed tube 11 towards the filter element, the sealing wall 31 slides deeper into the groove 30 and a parallel to the sealing wall 31 extending lip 32 projects into the narrowing of the opening 9 and seals it.

In FIG. 8 sealing members 12 en 13 are shown. For seal 13 an alternative location is shown in phantom for a further alternative wherein the lip 32 is absent. In the closed position the wall 33 rests sealingly against the sealing member 3. The opening 9 then needs no narrowing. A further alternative is feasible, wherein lip 32 does not penetrate opening 9, but a groove 34 at the inner side of the opening 9 (shown in phantom; lip 32 is then positioned opposite groove 34).

The sealing member 12 and/or 13 can also be located elsewhere. Parts can be changed between the filter element 7 and feed tube 11.

The embodiment of FIG. 8 is e.g. suited with an opening 9 that is interrupted open along its length (in top view), e.g. provided by a number of openings with mutual spacing.

In stead of a groove the relating wall of the filter element 7 can have an upright edge or wall or such. The feed tube 11 can then function without a projecting or upright wall, such as the sealing wall 31.

Thus the sealing means have some kind of telescoping feature. Ensuring of the medium tight connection of the feed tube 11 to the wall of the filter element, both in the open and closed position, can however also be ensured in a different manner, e.g. by a bellows element or different easily deformable element that is mounted to the filter element 7 by using mounting means. The advantage of a rigid element as used in FIG. 2 is however, that cleaning and/or assembling is made easier, while the opened or closed position can easily be recognised.

Figure 3:
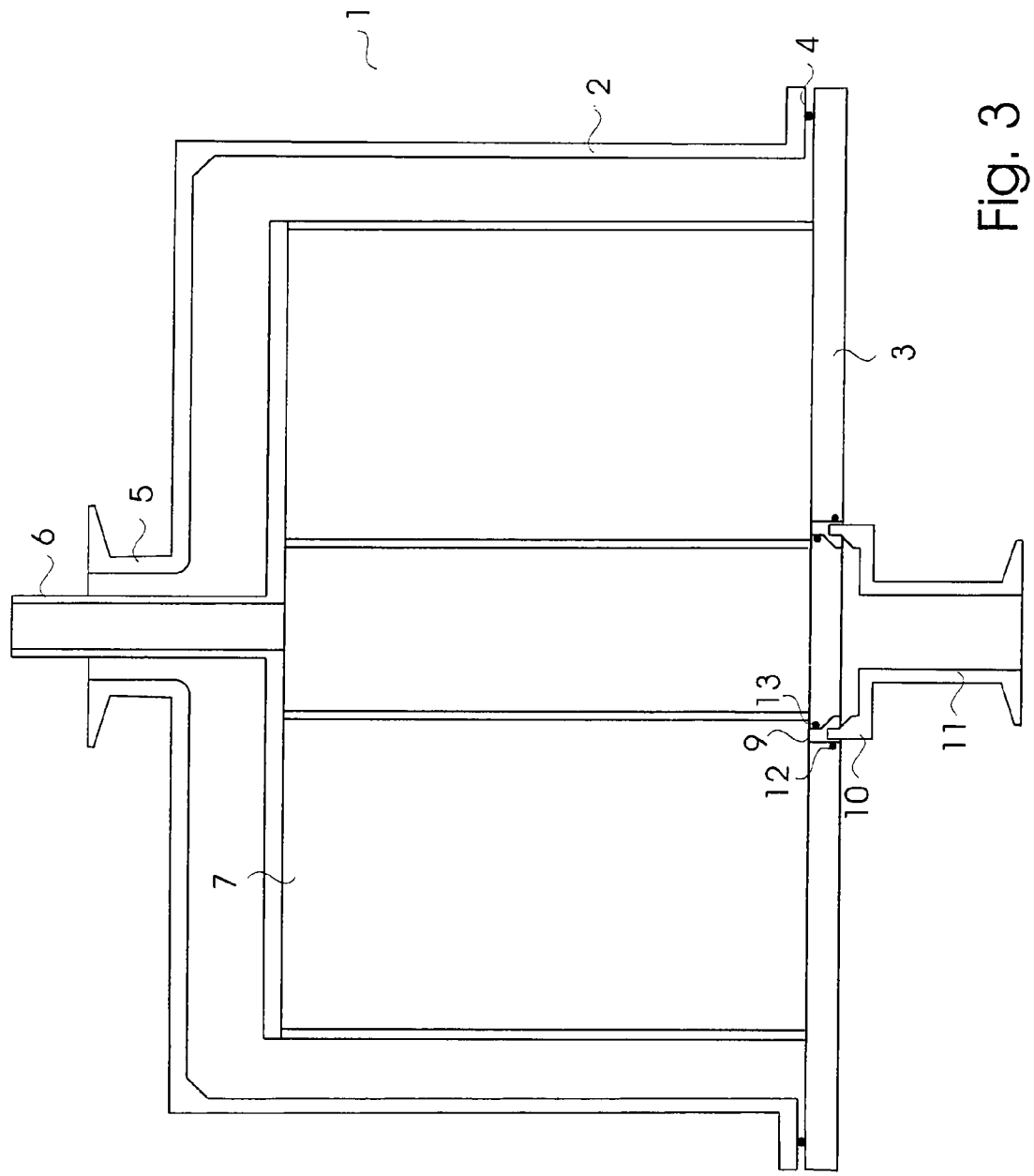
Figure 4:
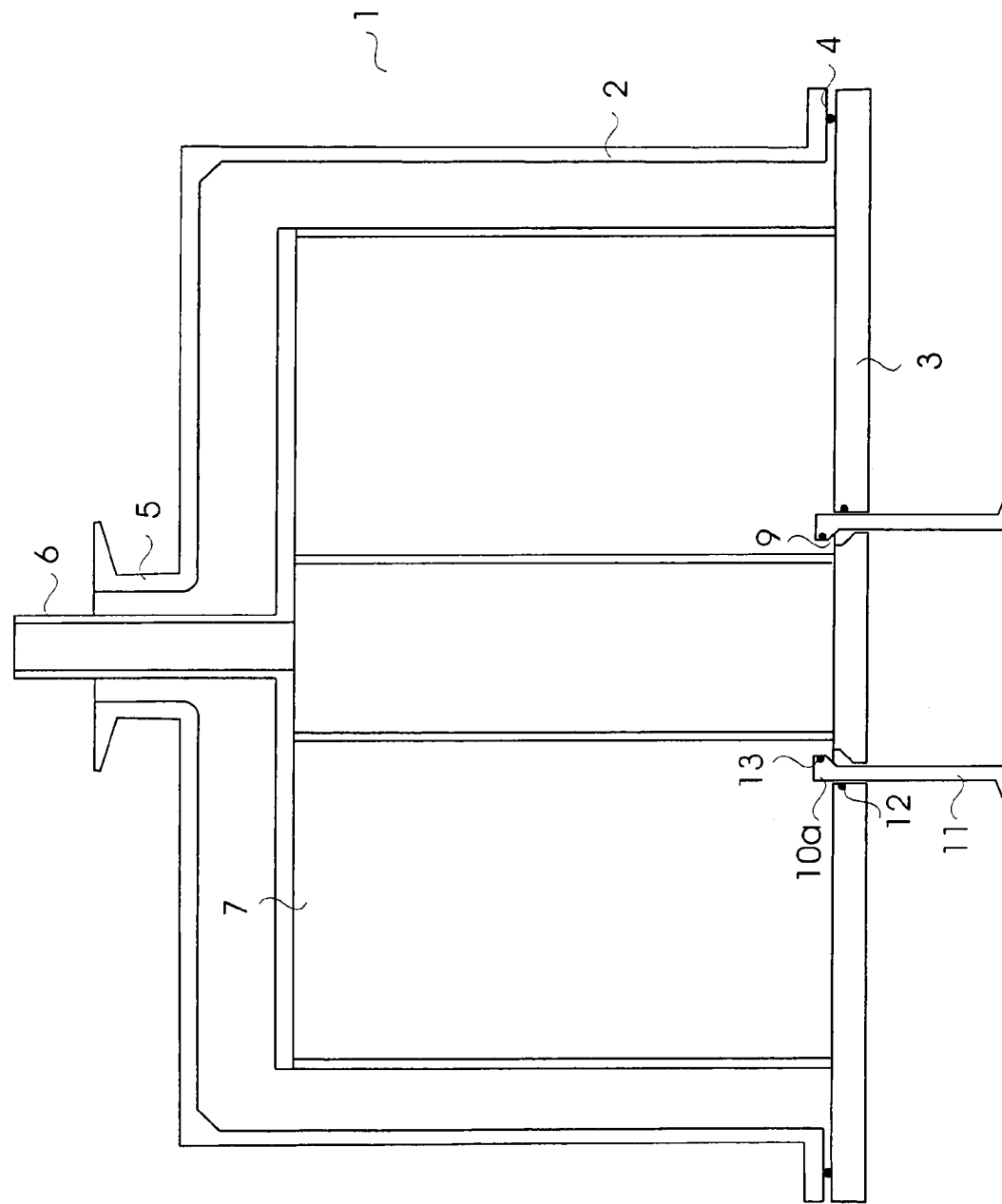

FIG. 3 shows an embodiment wherein the exit 6 is at the same side as the inlet 5 and (concentric) inside it. At the opposite side the filter element 7 contains the till opening 9. FIG. 4 is a variant to FIG. 3, wherein the co-operation between the fill opening 9 and the feed tube 11 is changed. By moving away from the filter element 7 of the feed tube 11, the fill opening 9 is now closed. If the fill opening 9 is opened, the sealing means 10a at the feed tube 11 project into the with matrix filled space of the filter element. The widening 10 at the fill tube 11 is now absent.

Figure 5:
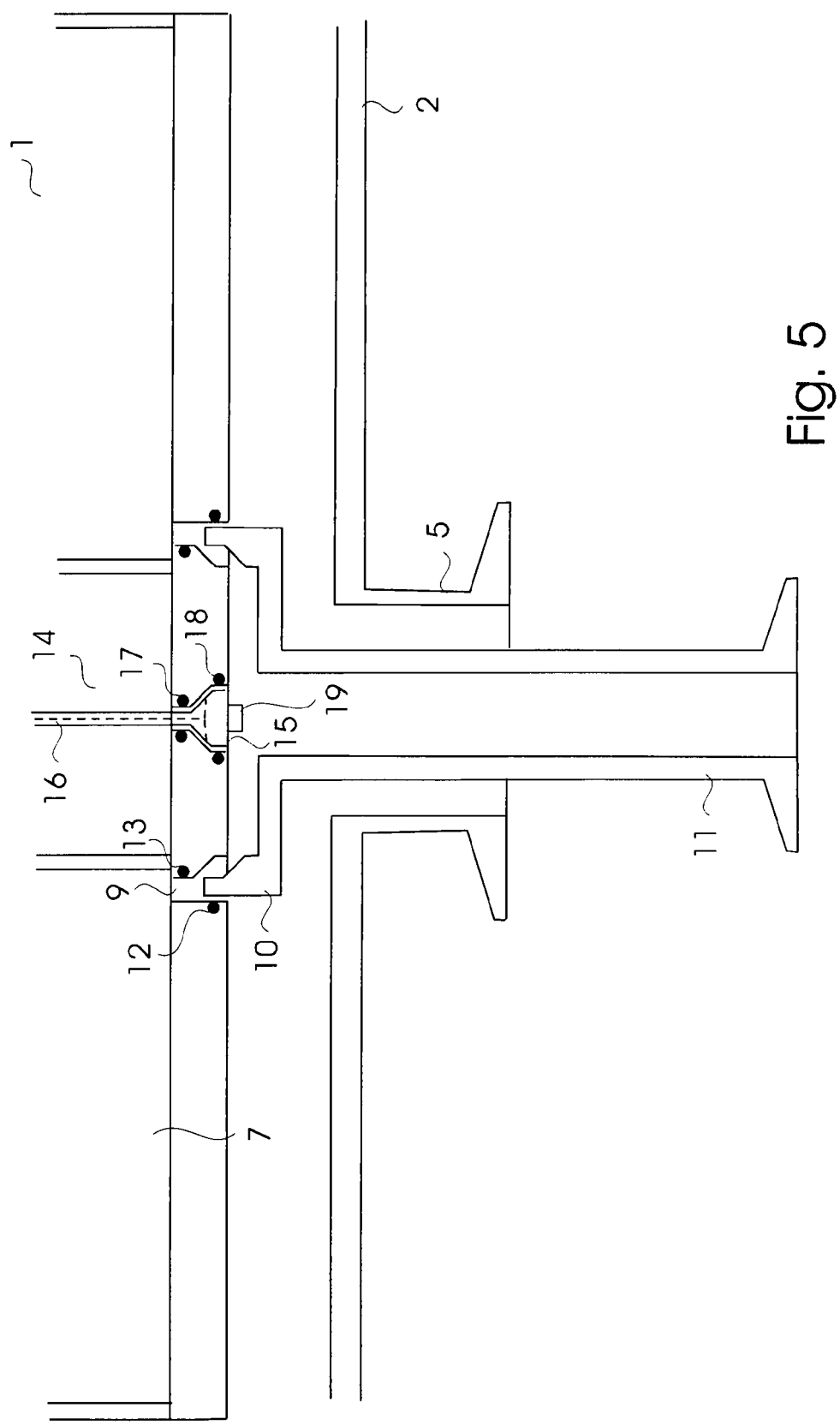
FIG. 5 shows a detail of an embodiment base don FIG. 2.

FIG. 5 shows the lower part of FIG. 2, to which a flushing element 14 is added. The flushing element 14 comprises a separately, conically shaped sealing element 15 that is seated in a similar shaped opening in the wall of the filter element 7. The sealing element 15 contains dispensing nozzles to which a supply tube 16 is connected. Sealing members for the sealing element 15 are indicated by 17 and 18. 19 indicates the location of a sensor (e.g. pressure sensor) to determine the fill level of the filter element 7 during filling. With closed fill opening 9 and emptied feed tube 11, one can (axially) lower the sealing element 15 into the feed tube 11 and supply flushing medium through the supply tube 16 and thus spray/jet against the inner wall of the feed tube 11 from the nozzles.

Figure 6:
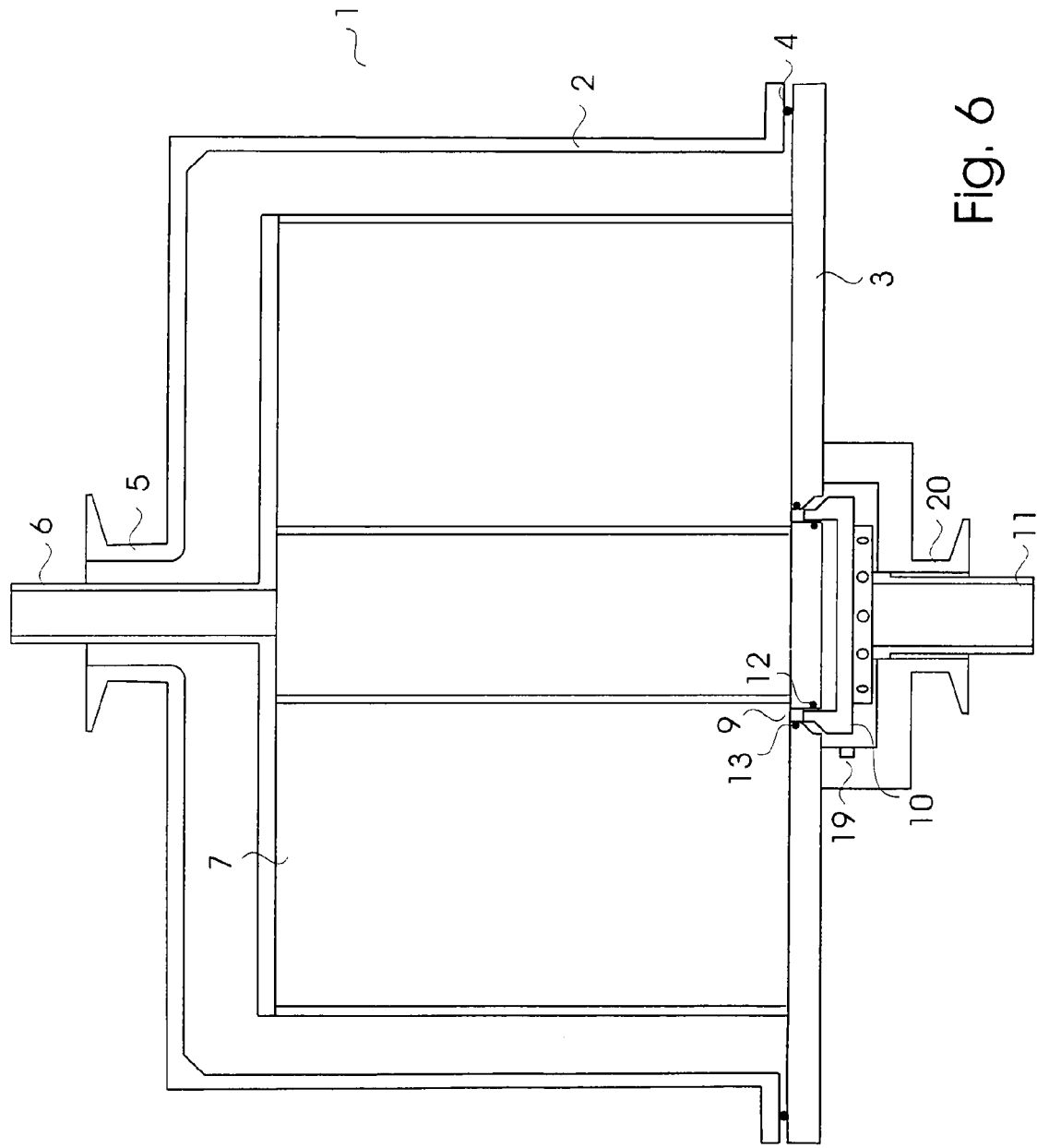
Figure 7A:
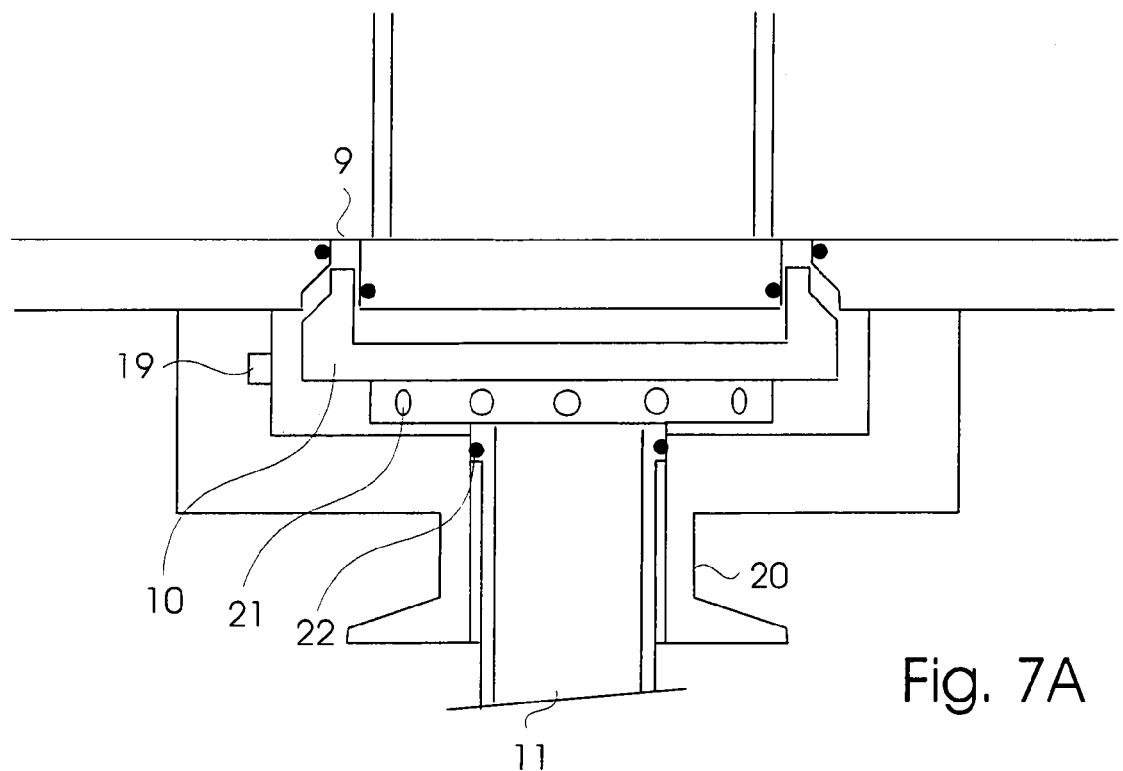
FIG. 7A and B show a detail of the embodiment of FIG. 6 in the fill and flush position.
Figure 7B:
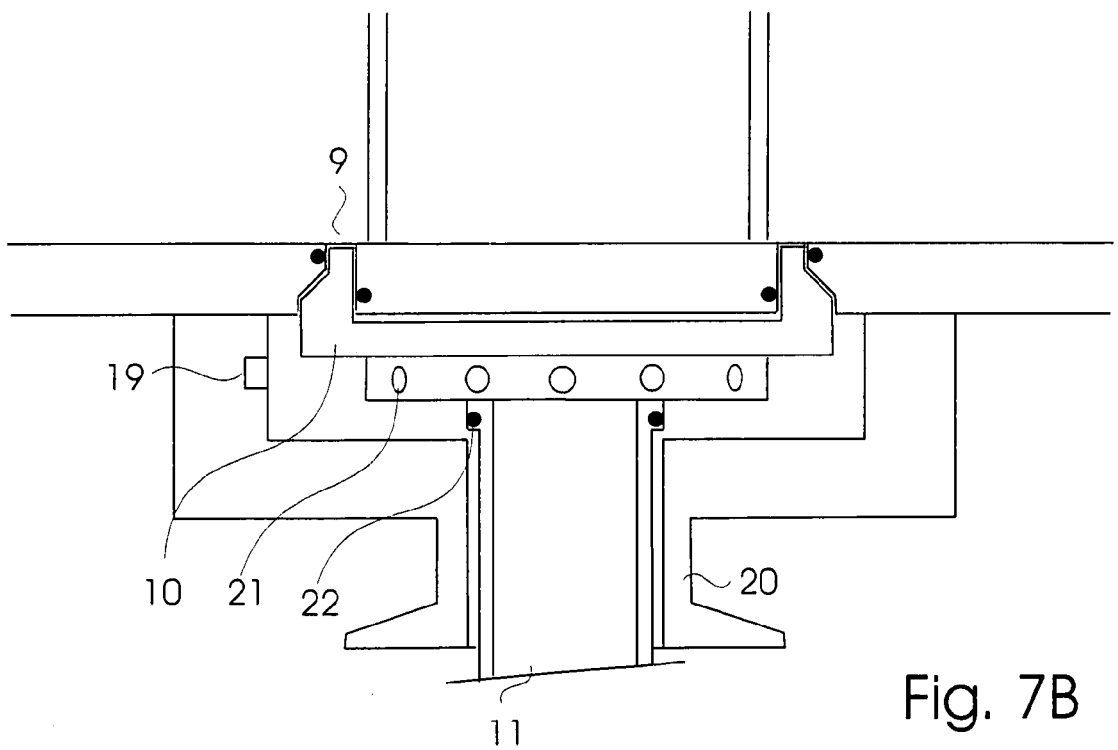

FIG. 6 shows a variant to FIG. 3. A flushing tube 20 is added, inside which the feed tube 11 is (preferably concentrically) present. The sensor 19 is located at a different location. From this embodiment the lower side is shown more in detail in FIGS. 7A and B. While filling the filter element with matrix (FIG. 7A), matrix flows from the feed tube 11 through openings 21 towards fill opening 9. Through a radial enlargement or projection and a sealing member 22 the feed tube sealingly connects to the flushing tube 20. If the fill opening 9 is closed (FIG. 7B), the feed tube 11 is displaced towards the filter element 7. The enlargement and sealing member 22 are (axially) moved away from the flushing tube 20. Flushing medium is through the annular space between the tubes 11 and 20 axially supplied, flows radially outward and then through the openings 21 into the feed tube 11 to axially flow back through it.

Thus the embodiments according to FIGS. 5 and 6 provide a flushing feature by using a sealing feature which by displacing and/or rotating releases dispensing means, wherein said sealing feature keeps the flushing agent supply sealed during filling with matrix. The sealing feature can comprise a conical or enlarged or projecting part.

Different embodiments also belong to the invention. E.g. wherein, e.g. according to WO 03/059488 A3, the filter body is provided with an additional discharge opening, e.g. at the side axially opposite the side with the supply opening 5 and such that through said opening 5 supplied medium can leave the filter body 1 without flowing through the matrix. Preferably a radial flow space is both below and above the filter element 7 present. Thus one can ensure that only a part of the supplied medium flows through the matrix, while the rest flows axially and/or tangentially externally along the external case.

All described or in the drawing illustrated features, or its functional equivalent, provide as such or in arbitrary combination the subject of this invention, also independent from their composition in the claims.

E.g. the hollow core, free from matrix, is at least partly filled with a material which is impermeable to the to the opening fed medium, such that the free space within said core is made as small as possible and there is only a limited flow through sectional area available to the medium to be able to flow towards the exit 6 after leaving the matrix.

In an alternative the filter body 1 is designed such that the medium flows radially from the inside to the outside through the matrix. Also an embodiment is possible, wherein the parts above and below or left and right are mutually changed. Also an embodiment is possible, wherein a flow direction is opposite as disclosed above.

The above mainly relates to a filter body wherein the medium flows radially through the matrix. Also embodiments belong to the invention, wherein the medium flows axially or axially/radially through the matrix. A the matrix delimiting top or bottom wall can allow passage of medium, in addition to or as an alternative for the medium permeability of one or more side walls. For an axially flown through matrix of the filter body, the top and bottom wall, delimiting the matrix, will allow passage of medium, while the side walls, delimiting the matrix, will not allow passage of medium.

The invention is specifically designed for bio molecules, such as proteins, DNA plasmids or viruses. Isolating, separating, fractionating or removing (filtering) of unwanted components (such as contamination or smaller molecules) are possible applications.

The invention claimed is:

1. Filter system provided by a chromatography column for filtering of a substance present in a fluid, the substance comprising at least one of molecules and proteins, the system containing a filter element which is filled with an exchangeable filter medium and the filter system is provided with fill means with a single feed tube external from the filter system which feed tube is connected to an across the filter system distributed fill element, the filter element has a cavity which contains the filter medium, said cavity has a torus shape providing a fixed central, filter medium free axial channel and said cavity is axially delimited by a first and a second fixed end wall, which are fluid impermeable, and is radially delimited by two concentrically within each other located fixed side walls, which are fluid permeable, the inner side wall of which delimits at its inner side said central axial channel, the outer side wall of which delimits at its outer side an annular, axial flow space within the filter system, which axial flow space connects to a first opening in the filter element to communicate to the outside of the filter element, and which central channel is permanently sealed by a fixed inner land area of the first end wall and connects to a second opening in the second end wall to communicate to the outside of the filter element, such that flow of fluid between the annular axial flow space and the central axial channel passes radially through the filter element, the fill element has a gap like fill opening connecting to the cavity of the filter element and provided in the first fixed end wall sealing the central axial channel, which gap like fill opening extends completely around the central channel such that around the central channel a closed loop shaped annular fill opening of fixed dimensions is provided which completely extends around and encloses said fixed inner land area of the first end wall and separates said fixed inner land area from the rest of the first end wall, the single feed tube is connected to said gap like fill opening such that filter medium flowing through the feed tube during filling of the filter system with filter medium, flows exclusively through the gap like fill opening and then into the cavity of the filter element, and the single feed tube is sealingly connected to the filter system by permanent sealing means providing a sealing skirt surrounding the gap like fill opening at its radial outer side, the gap like fill opening is opened and closed by movable sealing means engaging the gap like fill opening from the side of the first end wall opposite the side facing the cavity of the filter element.

2. The filter system of claim 1, wherein the movable sealing means have a closed loop shaped annular shape corresponding to the shape of the gap like fill opening and engaging the gap like fill opening and extending around and enclosing said fixed inner land area.

3. The filter system of claim 2, wherein the gap like fill opening has opposite walls extending towards each other, thus providing a narrowing flow through opening and the movable sealing means have a shape matching to the shape of the gap like fill opening and penetrate into the gap like fill opening to seal it.

4. Filter system provided by a chromatography column for filtering of a substance present in a fluid, the substance comprising at least one of molecules and proteins, the system containing a filter element which is filled with an exchangeable filter medium and the filter system is provided with fill means with a single feed tube external from the filter system which feed tube is connected to an across the filter system distributed fill element, the filter element has a cavity which contains the filter medium, said cavity has a torus shape providing a fixed central, filter medium free axial channel and said cavity is axially delimited by a first and a second fixed end wall, which are fluid impermeable, and is radially delimited by two concentrically within each other located fixed side walls, which are fluid permeable, the inner side wall of which delimits at its inner side said central axial channel, the outer side wall of which delimits at its outer side an annular, axial flow space within the filter system, which axial flow space connects to a first opening in the filter element to communicate to the outside of the filter element, and which central channel is permanently sealed by a fixed inner land area of the first end wall and connects to a second opening in the second end wall to communicate to the outside of the filter element, such that flow of fluid between the annular axial flow space and the central axial channel passes radially through the filter element, the fill element has a gap like fill opening connecting to the cavity of the filter element and provided in the first fixed end wall sealing the central axial channel, which gap like fill opening extends completely around the central channel such that around the central channel a closed loop shaped annular fill opening of fixed dimensions is provided which completely extends around and encloses said fixed inner land area of the first end wall and separates said fixed inner land area from the rest of the first end wall, the single feed tube is connected to said gap like fill opening such that filter medium flowing through the feed tube during filling of the filter system with filter medium, flows exclusively through the gap like fill opening and then into the cavity of the filter element, and the single feed tube is sealingly connected to the filter system by fixed sealing means providing a sealing skirt surrounding the gap like fill opening at its radial outer side, the gap like fill opening is opened and closed by movable sealing means engaging the gap like fill opening from the side of the first end wall opposite the side facing the cavity of the filter element and the movable sealing means have a closed loop shaped annular shape corresponding to the closed loop annular shape of the gap like fill opening and engaging the gap like fill opening and extending around and enclosing said fixed inner land area.

5. The filter system of claim 4, wherein the gap like fill opening has opposite walls extending towards each other, thus providing a narrowing flow through opening and the movable sealing means have a shape matching to the shape of the gap like fill opening and penetrate into the gap like fill opening to seal it.

6. Filter system provided by a chromatography column for filtering of a substance present in a fluid, the substance comprising at least one of molecules and proteins, the system containing a filter element which is filled with an exchangeable filter medium and the filter system is provided with fill means with a single feed tube external from the filter system which feed tube is connected to an across the filter system distributed fill element, the filter element has a cavity which contains the filter medium, said cavity has a torus shape providing a fixed central, filter medium free axial channel and said cavity is axially delimited by a first and a second fixed end wall, which are fluid impermeable, and is radially delimited by two concentrically within each other located fixed side walls, which are fluid permeable, the inner side wall of which delimits at its inner side said central axial channel, the outer side wall of which delimits at its outer side an annular, axial flow space within the filter system, which axial flow space connects to a first opening in the filter element to communicate to the outside of the filter element, and which central channel is permanently sealed by a fixed inner land area of the first end wall and connects to a second opening in the second end wall to communicate to the outside of the filter element, such that flow of fluid between the annular axial flow space and the central axial channel passes radially through the filter element, the fill element has a gap like fill opening connecting to the cavity of the filter element and provided in the first fixed end wall sealing the central axial channel, which gap like fill opening extends completely around the central channel such that around the central channel a closed loop shaped annular fill opening of fixed dimensions is provided which completely extends around and encloses said fixed inner land area of the first end wall and separates said fixed inner land area from the rest of the first end wall, the single feed tube is connected to said gap like fill opening such that filter medium flowing through the feed tube during filling of the filter system with filter medium, flows exclusively through the gap like fill opening and then into the cavity of the filter element, and the single feed tube is sealingly connected to the filter system by fixed sealing means providing a sealing skirt surrounding the gap like fill opening at its radial outer side, the gap like fill opening is opened and closed by movable sealing means engaging the gap like fill opening from the side of the first end wall opposite the side facing the cavity of the filter element and the movable sealing means have a closed loop shaped annular shape corresponding to the closed loop annular shape of the gap like fill opening and engaging the gap like fill opening and extending around and enclosing said fixed inner land area and having a sealing projection penetrating the gap like fill opening to tightly fit into it and thus to seal it.

7. The filter system of claim 6, wherein the gap like fill opening has opposite walls extending towards each other, thus providing a narrowing flow through opening and the sealing projection of the movable sealing means has opposite walls having a shape matching to the shape of the gap like fill opening and penetrate into the gap like fill opening to tightly fit into it and thus to seal it.

8. A filter system comprising:
a filter body having an inlet opening and a discharge opening;
a filter element contained within said filter body, said filter element having concentric fluid-permeable inner and outer sidewalls extending between opposite fluid-impermeable end walls, said filter element being adapted to retain therein an exchangeable filter medium,
wherein a radial flow space is defined between one of said end walls of the filter element and the filter body, an axial flow space is defined between said outer sidewall of the filter element and said filter body, and a central axial channel is defined by said inner sidewall of the filter element and a central fluid-impermeable land area at one end thereof, such that fluid to be filtered flowing from said inlet opening to said discharge opening is directed radially through said filter element;
a fill opening extending through one of said end walls of the filter element and surrounding said central axial channel; and
a single, axially movable feed tube having at one end a sealing wall configured and arranged for selective sealing engagement with said fill opening, thereby opening or closing said fill opening, wherein an open condition of the fill opening establishes a fluid connection between said fill tube and said filter element whereby filter medium can be exchanged.

* * * * *